United States Patent [19]

Seper et al.

[11] Patent Number: 5,206,391
[45] Date of Patent: Apr. 27, 1993

[54] PROCESS FOR THE PREPARATION OF HALOPHTHALIC ANHYDRIDES

[75] Inventors: Karl W. Seper, Youngstown; Edward J. Colman, Niagara Falls; David Y. Tang, E. Amherst; Mary K. Cocoman, Grand Island; Harry E. Buckholtz, Lewiston, all of N.Y.

[73] Assignee: Occidental Chemical Corporation, Niagara Falls, N.Y.

[21] Appl. No.: 751,841

[22] Filed: Aug. 29, 1991

Related U.S. Application Data

[63] Continuation-in-part of Ser. No. 405,606, Sep. 11, 1989, Pat. No. 5,049,682.

[51] Int. Cl.$^5$ ............................................. C07D 307/74
[52] U.S. Cl. ................................. 549/246; 549/247; 558/415; 562/849; 562/853; 562/855
[58] Field of Search ............................... 549/246, 247

[56] References Cited

U.S. PATENT DOCUMENTS

| | | | |
|---|---|---|---|
| 4,517,372 | 5/1985 | Tang | 549/246 |
| 4,559,405 | 12/1985 | Telschow | 549/240 |
| 4,560,772 | 12/1985 | Telschow et al. | 549/240 |
| 4,560,773 | 12/1985 | Telschow | 549/240 |
| 4,792,618 | 12/1988 | Bieron et al. | 560/127 |
| 5,003,088 | 3/1991 | Spohn et al. | 549/246 |
| 5,049,682 | 9/1991 | Tang et al. | 549/246 |

OTHER PUBLICATIONS

Bergmann, J. Amer. Chem. Soc. 64, 176 (1942).
Skvarchenko, V. R., Russian Chemical Reviews, Nov. 1963 vol. 32, No. 11, pp. 571-589.
Goldfinger, Noyes, and Wen; J. Amer. Chem. Soc. 91 (14), 4003-4, 1969.
O. Ruff, W. Menzel (Z. Anorg. Allgem. Chem. 202 (1931) 49/61, 57).
Izv. Akad Nauk SSSR, Ser. Khim (6) 1315-20, 1970 CA103 (25):214656n.
Izv. Akad Nauk SSSR, Ser. Khim (8) 1709-15, 1985 CA74 (17):87221x.

*Primary Examiner*—Thurman K. Page
*Assistant Examiner*—Jyothsna Venkat
*Attorney, Agent, or Firm*—Wayne A. Jones; Arthur S. Cookfair

[57] ABSTRACT

A process for the preparation of a halophthalic anhydride, such as chlorophthalic anhydride, comprising the liquid phase reaction of bromine with a halogen substituted hexa- or tetra-hydrophthalic anhydride to produce halophthalic anhydride and gaseous HBr, and reacting the gaseous HBr with chlorine to regenerate bromine.

15 Claims, No Drawings

PROCESS FOR THE PREPARATION OF HALOPHTHALIC ANHYDRIDES

BACKGROUND OF THE INVENTION

This application is a continuation-in-part of U.S. application Ser. No. 07/405,606, filed Sep. 11, 1989 now U.S. Pat. No. 5,049,682.

This invention relates to a process for the preparation of halophthalic anhydrides by the bromine-catalyzed dehydrogenation of halogen substituted saturated or partially saturated phthalo compounds, such as halogen-substituted tetrahydro or hexahydro phthalic anhydrides. Halophthalic anhydrides are useful chemical intermediates for the synthesis of various commercial products, including polymers, dyes and plasticizers.

The increasing importance of high performance polyimides has led to an increased interest in halophthalic anhydrides. The latter are particularly useful as intermediates for the preparation of dianhydride monomers, such as oxydiphthalic anhydride which may be co-polymerized with a suitable diamine to form a condensation polyimide. The preparation of dianhydride monomers for the high performance polymer industry requires halophthalic anhydrides of very high purity, since the presence of even what normally would be considered as minor amounts of impurities would degrade the polymer product and perhaps render the product unsuitable for certain uses.

Halophthalic anhydrides may be prepared by the reaction of bromine with halo-substituted saturated or partially saturated phthalic anhydrides, such as halotetrahydrophthalic anhydride or gem-dihalohexahydrophthalic anhydride, at temperatures in excess of 200° Celsius. However, this approach has been found to result in relatively low yields and is in general, uneconomical.

Various other methods for the preparation of phthalic anhydrides by the dehydrogenation of saturated or partially saturated cyclic anhydrides are known in the chemical literature.

Bergmann J. Amer. Chem. Soc. 64, 176 (1942) discloses the aromatization of tetrahydrophthalic anhydride products of Diels-Alder reactions. The author discloses that dehydrogenation occurred when the tetrahydrophthalic anhydride product is boiled in nitrobenzene. However, it is further disclosed that dehydrogenation does not occur when p-bromonitrobenzene, p-chloronitrobenzene, or m-dinitrobenzene in xylene is employed. Moreover, it has been found that when the dihalohexahydrophthalic anhydrides are dehydrogenated in nitrobenzene, a portion of the nitrobenzene is reduced to aniline. The aniline reacts with the anhydride group of either the starting material or product to form imides and thus lower the yield of desired product.

U.S. Pat. No. 4,560,772 to Telschow discloses the reaction of 4-methyltetrahydrophthalic anhydride with excess sulfur and a catalytic amount of zinc oxide and 2-mercaptobenzothiazole to produce 4-methylphthalic anhydride and hydrogen sulfide.

U.S. Pat. Nos. 4,560,773 and 4,559,405 to Telschow disclose the preparation of substituted phthalic anhydrides by reaction of bromine with an alkyl or aryl-substituted tetrahydrophthalic anhydride, especially 4-methyltetrahydrophthalic anhydride, in the presence of an acid acceptor, such as pyridine or dimethylformamide. In the working examples, U.S. Pat. No. 4,560,773 discloses yields of 62-80% and purity of only 90-95% even after vacuum distillation. According to the patentee, the yield and purity of the desired end product would be even lower if the reaction were carried out in the absence of an acid acceptor.

U.S. Pat. No. 4,517,372 to Tang, disclose a process for the preparation of 4-fluorophthalic anhydride by dehydrogenation of gem-, difluoro- or gem-chlorofluoro-hexahydrophthalic anhydrides in the presence of a dehydrogenation catalyst, such as palladium.

Skvarchenko et al., Obshchei Khimii, Vol. 30, No. 11. pp. 3535-3541 disclose the aromatization of chloro-substituted tetrahydrophthalic anhydride by heating with phosphorus pentoxide. In the aromatization process described, however, decarboxylation also occurs with the formation of the corresponding chloro-substituted benzene compound. The preparation of various other tetrahydrophthalic acids and anhydrides and various methods for dehydrogenation and aromatization thereof are reviewed by Skvarchenko in Russian Chemical Review. No. 1963, pp. 571-589.

U.S. Pat. No. 5,003,088 to Spohn, Sapienza and Morth, is directed to the preparation of halophthalic anhydrides by the reaction of chlorine with halotetrahydrophthalic anhydride or gem-dihalohexahydrophthalic anhydride at temperatures of 200° Celsius and higher.

Although the chemical literature discloses a variety of methods for the preparation of substituted phthalic anhydrides, it will be appreciated that a need continues to exist for a more economical and efficient dehydrogenation process, suitable for the preparation of high purity halophthalic anhydrides.

The process disclosed herein involves the preparation of halogen substituted phthalo compounds, such as halophthalic anhydrides, by the liquid phase aromatization reaction of the corresponding halo-substituted saturated or partially saturated compounds, such as halo-tetrahydro-phthalic anhydride or gem-dihalohexahydrophthalic anhydride with bromine. The use of bromine in the liquid phase aromatization reaction to prepare halo-substituted phthalo compounds has been found to be substantially more efficient than the analogous use of chlorine. However, it will be appreciated that the use of bromine involves some economic disadvantages resulting from the higher cost of bromine and the problem of limited uses or reapplications of the HBr reaction by-product.

It is known that high purity HBr may be reacted with gaseous chlorine to form bromine and HCl (Goldfinger, Noyes, and Wen; J. Amer. Chem. Soc., 91(14), 4003-4, 1969). However, it has not been known heretofore that crude HBr off-gas from an industrial bromination process could be reacted with gaseous chlorine in an economic and efficient manner to permit the recovery of recyclable bromine and HCl.

It is a primary object of this invention to provide a process for the preparation of halophthalo compounds by a liquid phase bromine aromatization reaction that overcomes the economic disadvantages heretofore associated with the use of bromine in such reactions. It is a further object to provide such a process wherein the bromine reactant is regenerated and recovered in a non-aqueous reaction.

SUMMARY OF THE INVENTION

It has now been found that a halogen substituted phthalo compound of the formula

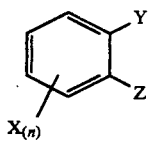

wherein each X is independently F-, Cl-, Br-, or I-, n is 1 or 2, and Y and Z are Cn, COBr, COCl, or COF, or Y and Z taken together form an anhydride group, may be prepared efficiently and economically in high yield and purity by the steps of A) reacting bromine in a liquid phase reaction, at temperatures below 230° Celsius, with a halogen substituted hexa-, or tetra-, hydrophthalo reactant of the formula

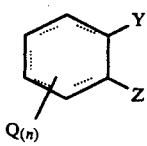

wherein Q is monohalo and is the same as X or is gem-dihalo, wherein at least one halogen is the same as X, and n is the same number as in formula I, and Y and Z are the same as in Formula I, above, to produce the phthalo compound of Formula I, and by-product gaseous HBr; and B) reacting the gaseous HBr with chlorine to produce HCl and bromine. When Q is monohalo, each monohalo is directly attached to a double bond carbon and when Q is gem-dihalo, the gem-dihalo is directly attached to a non-double bond carbon. When Y and Z are CN, COBr, COCl, or COF, the product of the bromine reaction may, in a known manner, be hydrolyzed to the dicarboxylic acid which, in turn, may be dehydrated to form the anhydride of formula I.

The re-oxidation of HBr by-product (Step B) may be carried out in a separate reaction vessel and the bromine produced may be recycled, stored, or used in a different reaction. Alternatively, the bromine recovery may be carried out in the same reaction vessel, in the vapor space above the liquid reaction mixture. In this case, chlorine gas is added to the vapor space, during the liquid phase reaction, to react with the exiting HBr. The bromine produced may be condensed back into the organic liquid phase to be reused.

If the bromine is recovered in a separate reaction vessel and not immediately recycled to react with the organic liquid phase, then the amount of bromine provided is preferably at least a stoichiometric amount, that is, two moles of bromine per mole of tetrahydro reactant, and most preferably about 10 percent in excess of that stoichiometric amount.

If the bromine recovery reaction is carried out in-situ, that is in the same reaction vessel, either sub-surface, or preferably, in the vapor space above the liquid reaction mixture, and the recovered bromine condensed and recycled into the liquid reaction mixture, the total of bromine and chlorine supplied to the process is preferably at least a stoichiometric amount, that is, two moles per mole of tetrahydro reactant, and most preferably about 10 percent in excess of that stoichiometric amount. The ratio of bromine (to the liquid phase): chlorine (to the gaseous phase bromine recovery) may vary; for example, from less than about 0.1:1 to about 10:1 or higher. The preferred ratio is about 1:1. In general, a lesser proportion of chlorine will result in a lower recovery of bromine and higher proportions of chlorine will be less efficient in terms of yield of the aromatized product.

DETAILED DESCRIPTION OF THE INVENTION

The starting reactants for the process of this invention, as represented by structural formula (II), above, are saturated and partially saturated halo-ortho-phthalo-hexa-, or tetra-hydroaromatic compounds including halotetrahydrophthalic anhydrides such as those of the formula

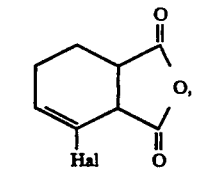

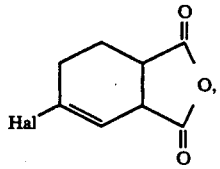

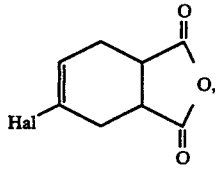

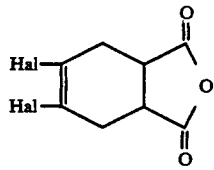

and the like, and gem-dihalohexahydrophthalic anhydrides such as those of the formulae

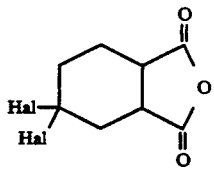

and the like, wherein Hal represents halogen; and the corresponding halotetrahydro- and gem-dihalohexahydro-ortho-phthalonitriles and ortho-phthaloyl dihalides. The preferred reactants are the saturated and partially saturated phthalic anhydrides.

Suitable reactants are available commercially or can be prepared by various known methods. For example, the Diels-Alder reaction of a maleic anhydride with a conjugated diene will produce an anhydride with a partially saturated six-membered ring.

Depending on the desired anhydride product, the conjugated diene and/or the maleic anhydride may be selected which contain the appropriate halogen substituents. The anhydride reactants that may be employed in the process of this invention include, for example:
4-chloro-1,2,3,6-tetrahydrophthalic anhydride;
4-fluoro-1,2,3,6-tetrahydrophthalic anhydride;
4-bromo-1,2,3,6-tetrahydrophthalic anhydride;
4-chloro-1,2,5,6-tetrahydrophthalic anhydride;
4-fluoro-1,2,5,6-tetrahydrophthalic anhydride;
4-bromo-1,2,5,6-tetrahydrophthalic anhydride;
4-chloro-1,2,3,6-tetrahydrophthalonitrile
4-fluoro-1,2,5,6-tetrahydrophthalonitrile
4-bromo-1,2,3,6-tetrahydrophthaloyl chloride
4-chloro-1,2,3,6-tetrahydrophthaloyl chloride
4,4-difluorohexahydrophthalic anhydride;
4,4-dichlorohexahydrophthalic anhydride;
4-chloro-4-fluorohexahydrophthalic anhydride;
4,4-dibromohexahydrophthalic anhydride;
4,4-difluorohexahydrophthaloyl chloride
4-chloro-4-fluorohexahydrophthalonitrile
3-chloro-1,2,5,6-tetrahydrophthalic anhydride;
3-fluoro-1,2,5,6-tetrahydrophthalic anhydride;
3-bromo-1,2,5,6-tetrahydrophthalic anhydride;
3,3-difluorohexahydrophthalic anhydride;
3,3-dichlorohexahydrophthalic anhydride;
3,3-dibromohexahydrophthalic anhydride;
3,3-difluorohexahydrophthaloyl dichloride
4,5-dichloro-1,2,3,6-tetrahydrophthalic anhydride;
4,5-difluoro-1,2,3,6-tetrahydrophthalic anhydride;
4,5-dibromo-1,2,3,6-tetrahydrophthalic anhydride;
3,4-dichloro-1,2,5,6-tetrahydrophthalic anhydride;
3,4-difluoro-1,2,5,6-tetrahydrophthalic anhydride.

The corresponding iodo compounds may be employed, but are generally less stable and are not preferred.

When the starting reactant is a saturated or partially saturated halogen substituted ortho-phthalonitrile or phthaloyl dihalide, the reaction product may be converted to an anhydride in a known manner. Thus, when a halogen substituted tetrahydrophthalonitrile, or gem dihalohexahydrophthalonitrile, is reacted with a bromine, in accordance with the invention, the resulting halogen substituted phthalonitrile may be hydrolyzed, in a known manner, for example, using aqueous acid, to form the dicarboxylic acid, which is then dehydrated chemically or thermally to form the corresponding halophthalic anhydrides. In addition, the halophthalonitrile may be used as an intermediate to prepare the corresponding amides or other useful end products. Using the halogen substituted tetrahydrophthaloyl dihalide, or gem-dihalohexahydrophthaloyl dihalide in the bromination reaction, results in the formation of the corresponding halo-phthaloyl dihalide which may then be hydrolyzed in a known manner to the corresponding diacid which, in turn, may be chemically or thermally dehydrated to form the corresponding anhydride. Furthermore, the halo-phthaloyl dihalides may be employed as intermediates in the formation of various esters, by alcoholysis, or in the formation of the corresponding amides by ammonolysis.

In addition to the anhydride reactants and products set forth, the applicability of the present invention to various equivalent reactants and products is contemplated. Contemplated equivalents to the anhydride reactants and products of the invention include the corresponding dicarboxylic acids, salts such as alkali metal salts, esters such as phenyl or alkylesters, imides, diamides and the like.

The bromination process (Step A) is carried out in the liquid phase, either neat or in the presence of a solvent, at atmospheric pressure or under applied or autogenous pressure at temperatures ranging from about 0° to about 230° Celsius or slightly higher and preferably about 70° to about 170° Celsius. Lower temperatures, such as 30° C. and 40° C., can be used but they are not generally preferred due to long reaction times and/or lower yields. At temperatures substantially higher than about 230° Celsius, some degradation of the reaction or the product of reaction may appear. Moreover, when the reaction mixture is heated to temperatures in excess of about 170° C., it is important that the initial reaction with bromine occur at a temperature below about 170° C.

Solvents that may be employed are preferably substantially non-reactive to bromine as well as to the organic reactant and preferably are characterized by a boiling point greater than about 100° Celsius. Typical of the solvents that may be employed are bromobenzenes and chlorobenzenes. The most preferred solvent is monochlorobenzene. Lower boiling solvents, such as chloroform, carbon tetrachloride, or chlorinated ethanes may be advantageously employed when the process is carried out at lower temperatures, for example, in the presence of a free radical initiator.

The bromination process involves a free radical reaction which may be enhanced by the use of a free radical initiator such as visible or ultra-violet irradiation, or addition of catalytic amounts, typically less than about 5 percent by weight, based on weight of reactants, of initiators such as azo compounds, peroxides and the like. Typical azo compounds useful as free-radical initiators are azobis (alpha, gamma-dimethyl valeronitrile), 2,2'-azobis (2,4-dimethyl valeronitrile); and typical peroxides are benzoyl peroxide, diacetyl peroxide, diisopropyl peroxydicarbonate, lauroyl peroxide and the like. Azobisisobutyronitrile is particularly useful in the process of this invention. When the process is carried out in the presence of a free radical initiator, lower temperatures, typically in the range of about 0° to about 100° Celsius, may be employed.

When the process of Step (A) is carried out to substantial completion at a single temperature, or temperature range, it is preferred, based on yield and purity achieved, to carry it out at about 90° to 135° and preferably about 90° to 125° C. However, it has been found advantageous to carry out the reaction in at least two temperature stages, by adding the bromine reactant at temperatures of about 90° to 135° Celsius, and maintaining the temperature in that range until the bromine is substantially consumed and then increasing the temperature to above about 160° to remove any remaining dissolved HBr and convert any residual intermediates to the final product. When the bromine reactant has been substantially consumed at a lower temperature, the higher final temperature may, for example, be as high as about 250° without substantial deleterious effect. However, since temperatures greater than about 190° C. offer no particular advantage, it is preferred to employ final temperatures in the range of about 150°-160° to 190° Celsius.

In a preferred embodiment of the process of this invention, the addition of bromine to the reaction mixture is carried out in stages with associated increases in temperature. Preferably a major portion of the bromine, such as 65-80 percent, is added slowly while the reaction mixture is maintained at a temperature of about 90° to 125° Celsius until the bromine is substantially consumed. The temperature is then increased to about 130° to 145° and the remaining 20-35 percent of the bromine is added slowly while the temperature is maintained until the bromine is substantially consumed. The temperature is then increased to about 160°–175° and preferably maintained thereat for a period of time, such as about 3 to 8 hours to remove any remaining dissolved HBr and convert any residual intermediates to the final product.

During the reaction the exiting vapors may be condensed at a temperature sufficient to condense bromine, but allow HBr to escape to a separate reaction vessel for reaction with chlorine and recovery of $Br_2$. Alternatively, chlorine may be added to the vapor space above the liquid reaction mixture, to react with the gaseous HBr exiting the reaction. The bromine produced may be condensed and returned directly to the liquid reaction mixture.

The following specific examples are provided to further illustrate this invention and the manner in which is may be carried out. It will be understood, however, that the specific details given in the examples have been chosen for purposes of illustration and are not to be construed as a limitation on the invention. In the examples, unless otherwise indicated, all temperature are in degrees Celsius.

EXAMPLE 1

A mixture of 93 g (0.5 moles) of 4-chlorotetrahydrophthalic anhydride and 30 g of monochlorobenzene was heated and maintained at 105° C. TO 135° C. while 80 g (0.5 moles) of bromine was added over a three hour period. Simultaneously, chlorine gas (0.5 moles) was added to the vapor space above the organic liquid. As the HBr off-gas from the reaction of bromine with 4-chlorotetrahydrophthalic anhydride exited, it contacted the chlorine gas and the resultant bromine was condensed back into the organic liquid phase for reuse. A total of 36.45 g (0.5 moles) of chlorine were consumed during this time. The reaction mixture was finally heated to 165°–175° C. for an additional 5 hours. The crude reaction mixture was distilled resulting in isolation of 86% of 4-chlorophthalic anhydride.

EXAMPLE 2

The general procedure of Example I was repeated except that 0.05 moles of bromine and 0.95 moles of chlorine were used. The isolated yield of 4-chlorophthalic anhydride was 47%.

EXAMPLE 3

The general procedure of Example 1 was repeated except 0.1 moles of bromine and 1.40 moles of chlorine were used. The isolated yield of 4-chlorophthalic anhydride was 38%.

EXAMPLE 4

The general procedure of Example 1 was repeated except that the chlorine gas was added subsurface to the organic liquid phase. The distilled yield of 4-chlorophthalic anhydride was 68.75.

EXAMPLE 5

Provided as a comparative example, the aromatization reaction was run identical to Example 1 except no bromine was employed in the reaction mixture and the chlorine (0.5 moles) was added directly to the liquid reaction mixture. The nonisolated GC yield of this example was 21% of 4-chlorophthalic anhydride. The balance of organic reaction product was higher chlorinated species.

EXAMPLE 6

A mixture of 80 g 4-chlorotetrahydrophthalic anhydride (0.43 mole), 30 g of monochlorobenzene, and 0.24 g of Halcomid ® (a commercially available metal sequestering agent) was heated and maintained at about 115° C., with mixing, while 98.18 g of bromine (0.61 mole) was added, sub-surface, over a period of about 4 hours. The temperature was raised to about 135° C. and maintained thereat while an additional 39.2 g of bromine (0.23 mole) was added over a period of about 3 hours. The reaction mixture was then heated and maintained at about 175° to 195° C. for an additional 3–4 hours to assure completion of the reaction. GC analysis of the crude reaction product indicated 93.3% 4-chlorophthalic anhydride (GC area %; solvent free basis).

EXAMPLE 7–18

The procedure of Example 6 was repeated and the HBr off-gas from the liquid aromatization reaction mixture was passed through a water-cooled condenser, packed with glass beads, within which the off-gas was contacted with chlorine gas, in a ratio as shown in the table, below, to regenerate bromine. The resulting mixture, $Br_2$ and HCl, was passed through a jacketed, chilled flask, equipped with a chilled condenser, to condense the regenerated bromine. The remaining noncondensable acid gases were collected by passing to a water trap and 20% potassium hydroxide trap.

The regenerated bromine was collected in the chilled condenser and the bromine yield was determined form the weight of bromine collected and the weight of bromine fed to the aromatization reactor. Bromine purity was estimated from a density relation for bromine/chlorine mixtures, assuming chlorine to be the only appreciable impurity.

The collected results of Examples 6–18 are set forth in Table I, below:

TABLE I

| Example | Crude 4-xPAN* Yield (GC area %) | $Cl_2$:HBr | $Br_2$ Recovery (%) |
|---|---|---|---|
| 6 | 93.2 | NA | NA |
| 7 | 94.7 | 0.75 | 50.5 |
| 8 | 94.7 | 0.75 | 38.4 |
| 9 | 92.9 | 0.84 | 41.6 |
| 10 | 91.8 | 0.78 | 57.8 |
| 11 | 77.8 | 1.48 | 70.5 |
| 12 | 86.7 | 0.56 | 75.6 |
| 13 | 85.5 | 0.57 | 95.7 |
| 14 | 75.6 | 0.50 | 79.1 |
| 15 | 93.4 | 0.48 | 87.1 |
| 16 | 93.8 | 0.52 | 81.4 |
| 17 | 93.8 | 0.50 | 74.2 |
| 18 | 93.4 | 0.55 | 80.2 |

*4-Chlorophthalic Anhydride (containing less than 3.0% 4-bromophthalic anhydride

EXAMPLE 19

The procedure of Examples 6–18 is repeated except that the gaseous mixture of $Br_2$ and HCl, produced by the reaction of chlorine and HBr, was passed into 150 g monochlorobenzene to preferentially dissolve the $Br_2$ product. The resulting monochlorobenzene solution contained 93.3% of the bromine reactant.

We claim:

1. A process for the preparation of a halogen substituted phthalic anhydride of the formula

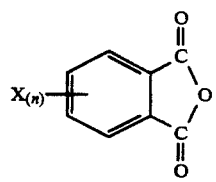

wherein X is independently F-, Cl-, Br-, or I-; and n is 1 or 2, which comprises a) reacting in the liquid phase at temperatures below about 230° Celsius, bromine with a halogen substituted hexa-, or tetra- hydrophthalo- reactant of the formula

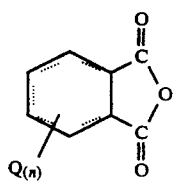

wherein Q is monohalo and is the same as X or is gem-dihalo, wherein at least one halogen is the same as X, and n is the same number as in formula I, with the proviso that each monohalo is directly attached to a double bond carbon and each gem-dihalo is directly attached to a non-double bond carbon and with the proviso that the initial reaction is carried out at a temperature below 170° Celsius to produce the halogen substituted phthalo compound, of Formula I, and gaseous HBr; and B) reacting the gaseous HBr with chlorine to produce bromine and HCl.

2. A process according to claim 1 wherein X is F, Cl, or Br.

3. A process according to claim 2 wherein the gaseous HBr product of Step B is reacted with chlorine gas in-situ in the liquid reaction mixture, to regenerate Br$_2$.

4. A process according to claim 2 carried out in a covered reaction vessel wherein the gaseous HBr product is reacted with chlorine gas within the reaction vessel, in the vapor space above the liquid phase, to regenerate Br$_2$ and the regenerated Br$_2$ is condensed and recycled to the liquid phase reaction mixture of Step A.

5. A process according to claim 2 wherein the gaseous HBr product of Step A is passed to a separate reaction vessel and reacted according to Step B in the gas phase, with chlorine, to produce bromine and HCl.

6. A process according to claim 5 wherein the bromine and HCl products of Step B are passed through a solvent wherein bromine is preferentially dissolved.

7. A process according to claim 6 wherein the solvent is monochlorobenzene.

8. A process according to claim 2 wherein the reaction of Step A is carried out initially at a temperature below about 125° C. and the temperature is subsequently increased to about 160° to 190° Celsius.

9. A process for the preparation of halogen substituted phthalic anhydrides of the formula:

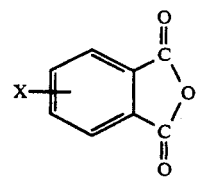

where each X is independently F-, Cl-, Br-, and n is 1 or 2, which comprises (A) reacting bromine with a halogen-substituted tetra-hydrophthalic anhydride reactant of the formula:

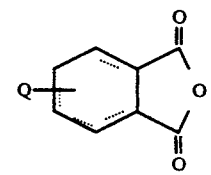

where Q is monohalo and is the same as X with the proviso that the monohalo is directly attached to a double bond carbon in the liquid phase at a temperature of 0° to 190° Celsius to produce the compound of Formula I and gaseous HBr, and (B) reacting the gaseous HBr with chlorine to produce bromine and HCl.

10. A process according to claim 9 wherein the gaseous HBr product of Step A is reacted with chlorine gas in-situ in the liquid reaction mixture to regenerate Br$_2$.

11. A process according to claim 9 carried out in a covered reaction vessel wherein the gaseous HBr product is reacted with chlorine gas within the reaction vessel, in the vapor space above the liquid phase, to regenerate Br$_2$, and the regenerated Br$_2$ is condensed and recycled to the liquid reaction mixture of Step A.

12. A process according to claim 9 wherein the gaseous HBr product of Step A is passed to a separate reaction vessel and reacted, according to Step B, in the gas phase, with chlorine, to produce bromine and HCl.

13. A process according to claim 12 wherein the bromine and HCl products of Step B are passed through a solvent wherein bromine is preferentially dissolved.

14. A process according to claim 13 wherein the solvent is monochlorobenzene.

15. A process for the preparation of a halogen-substituted phthalic anhydride of the formula:

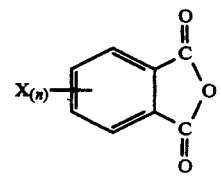

where each X is independently F-, Cl-, or Br- and n is 1 or 2, comprising the liquid phase reaction of bromine with a halogen substituted tetrahydrophthalic anhydride reactant of the formula:

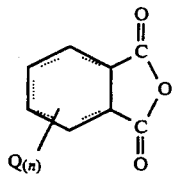

where Q is halo and is the same as X and n is the same number as in Formula I, with the proviso that each halo is directly attached to a double bond carbon, to produce the compound of Formula I and gaseous HBr and regenerating the bromine reactant; wherein the process comprises the steps of:

(A) adding the major portion of the bromine to a reaction mixture comprising the reactant of Formula II and maintaining the reaction mixture at a temperature of about 90° to 125° Celsius until the bromine is substantially consumed with concurrent formation of gaseous HBr therefrom;

(B) increasing the temperature to about 130° to 145° Celsius and maintaining thereat while the remaining portion of the bromine is added and substantially consumed with concurrent formation of HBr therefrom;

(C) increasing the temperature to about 150° to 190° Celsius to remove any remaining dissolved HBr from the liquid phase; and (D) reacting the gaseous HBr with chlorine to produce bromine and HCl.

* * * * *